(12) United States Patent
Chi et al.

(10) Patent No.: US 6,303,809 B1
(45) Date of Patent: Oct. 16, 2001

(54) ORGANOMETALLIC RUTHENIUM AND OSMIUM SOURCE REAGENTS FOR CHEMICAL VAPOR DEPOSITION

(75) Inventors: Yun Chi, No. 5, East Yuan, National Tsing Hua University, Hsinchu (TW); Feng Jen Lee; Chao-Shiuan Liu, both of Taipei (TW)

(73) Assignee: Yun Chi, Hsinchu (TW)

( * ) Notice: Subject to any disclaimer, the term of this patent is extended or adjusted under 35 U.S.C. 154(b) by 0 days.

(21) Appl. No.: 09/458,305

(22) Filed: Dec. 10, 1999

(51) Int. Cl.$^7$ .................................................. C07F 15/00
(52) U.S. Cl. ................................. 556/136; 427/252
(58) Field of Search .............................. 556/136; 427/252

(56) References Cited

U.S. PATENT DOCUMENTS 4,250,210  2/1981  Crosby et al. ................. 427/252

OTHER PUBLICATIONS

D. E. Trent et al., "Vapor Deposition of Pure Ruthenium Metal from Ruthenocene," *Inorganic Chemistry*, vol. 3, No. 7 (Jul. 1964), pp. 1057–1058.

F. Calderazzo et al., "Reactions of Some Metal Carbonyls with Chelating Compounds containing Active Protons, especially Schiff's Bases," *J. Chem. Soc.* (A) (1969), pp. 1378–1386.

M. L. Green et al. "Chemical Vapor Deposition of Ruthenium and Ruthenium Dioxide Films," *J. Electrochem. Soc.: Solid–State Science and Technology*, vol. 132, No. 11 (Nov. 1985), pp. 2677–2685.

C. J. Smart et al., "Chemical Vapor Deposition of Ruthenium and Osmium Films from Mono–and Bis–(cyclopentadienyl) Complexes as Precursors," *Mat. Res. Soc. Symp. Proc.*, vol. 363 (1995), pp. 207–212.

Y. Senzaki et al., "Chemical Vapor Deposition of Ruthenium and Osmium Thin Films Using (Hexafluoro– 2–butyne)tetracarbonylruthenium and –osmium," *Chem. Mater.* vol. 5 (1993), pp. 1715–1721.

S. Yamamichi et al., "A Stacked Capacitor Technology with ECR Plasma MOCVD (Ba,Sr)TiO$_3$ and RuO$_2$/Ru/TiN/TiSi$_x$ Storage Nodes for Gb–Scale DRAM's," *IEEE Transactions on Electron Devices*, vol. 44, No. 7 (Jul. 1997), pp. 1076–1081.

E. P. Boyd et al., "Chemical Vapor Deposition of Metallic Thin Films Using Homonuclear and Heteronuclear Metal Carbonyls," vol. 9 (1997), pp. 1154–1158.

J. M Lee et al., "Preparation of High Quality RuO$_2$ Electrodes for High Dielectric Thin Films by Low Pressure Metal Organic Chemical Vapor Deposition," *J. Vac. Sci. Technol. A*, vol. 16, No. 5 (Sep./Oct. 1998), pp. 2768–2771.

S–E. Park et al., "RuO$_2$ Thin Film Fabrication with Plasma–enhanced Chemical Vapor Deposition," *Thin Solid Films*, vol. 341 (1999), pp. 52–54.

D. Barreca et al., "A Ru(II) $\eta^3$–Allylic Complex as a Novel Precursor for the CVD of Ru–and RuO$_2$–Nanostructured Thin Films," *Langmuir*, vol. 15, No. 13 (1999), pp. 4537–4543.

J. Sankar et al., "Low Temperature Chemical Vapour Deposition of Ruthenium and Ruthenium Dioxide on Polymer Surfaces," *J. Mater. Chem.*, vol. 9 (1999), pp. 2439–2444.

*Primary Examiner*—Porfirio Nazario-Gonzalez
(74) *Attorney, Agent, or Firm*—Darby & Darby

(57) ABSTRACT

A series of organometallic complexes of the general formula [M(CO)$_2$L$_2$] was provided, wherein M is ruthenium or osmium metal, and L is a β-diketonate ligand RC(O)CHC(O)R$^1$ where each of R and R$^1$ is independently selected from the group consisting of atoms of the element, C, H, O and F. These ruthenium and osmium complexes possess enhanced volatility and thermal stability characteristics, and are very suitable for CVD applications. Also disclosed are CVD methods by using these ruthenium or osmium complexes as source reagents for deposition of Ru, Os, RuO$_2$, OsO$_2$, and other Ru- or Os-containing films such as mixed metal oxide materials BaRuO$_3$, SrRuO$_3$, Sr$_2$RuO$_4$ and Bi$_2$Ru$_2$O$_7$ or bimetallic alloys Pt/Ru and Pd/Ru.

8 Claims, No Drawings

ORGANOMETALLIC RUTHENIUM AND OSMIUM SOURCE REAGENTS FOR CHEMICAL VAPOR DEPOSITION

BACKGROUND OF THE INVENTION

1. Field of the Invention

The present invention relates in general to organometallic source reagents for chemical vapor deposition. More particularly, it relates to thermally decomposable ruthenium and osmium organometallic compounds and complexes which are useful in chemical vapor deposition processes, for formation of ruthenium, osmium, $RuO_2$, $OsO_2$, and other ruthenium- or osmium-containing films on substrates. The invention also relates to a method for forming a ruthenium- or osmium-containing film by chemical vapor deposition utilizing such compounds.

2. Description of the Related Arts

Chemical vapor deposition (hereafter indicated as "CVD") is widely used for the formation of ruthenium, osmium, $RuO_2$ and $OsO_2$ thin films on a variety of substrates. CVD is a particularly attractive method for forming films because it is readily scaled up to production runs, and because the electronic industry has a wide experience and suitable equipment that can be applied to CVD processes.

CVD processes require suitable source reagents which are sufficiently volatile to permit a rapid transport of their vapors into the CVD reactor. The source reagents, which may be called the precursors, should be thermally stable and relatively inert against oxygen and moisture in air at room temperature to allow long-term storage. They also should decompose cleanly in the CVD reactor to deposit high purity metal component at the desired growth temperature on the substrate.

Various ruthenium organometallic complexes have been proposed as source reagents for CVD applications, which include ruthenocene and its alkyl substituted derivative complexes, such as $Ru(C_5H_4Pr^i)_2$, and carbonyl complexes, such as $Ru(CO)_4$ (hfb), hfb=hexafluoro-2-butyne, $[(C_5H_5)Ru(CO)_2]_2$ and $Ru_3(CO)_{12}$; tris-β-diketonate complexes, such as $Ru(acac)_3$, $Ru(tfac)_3$ and $Ru(TMHD)_3$; and organometallic olefin complexes, such as bis(2,4-dimethylpentadienyl)ruthenium, bis(2,4-dimethyloxapentadienyl)ruthenium, $(\eta^6\text{-}C_6H_6)Ru(\eta^4\text{-}C_6H_8)$, $C_6H_8$=1,3-cyclohexadiene, and $Ru(C_3H_5)_2(COD)$, COD=1,4-cyclooctadiene. Although some of these compounds are liquids or relatively volatile low-melting solids, which are amenable to sublimation for gas-phase transport into the CVD reactor, most of them are high-melting solids and associate with fairly high decomposition temperature, or thermally unstable and reactive towards moisture and oxygen upon exposure to air, which make them difficult to store and handle. Selected physical properties of these known organometallic reagents are listed in Table 1.

TABLE 1

Selected physical properties of known organometallic ruthenium source reagents

| Compound | Melting Point (° C.) | Decomposition Temperature (° C.) | Sublimation Condition or Vapor Pressure (mmHg) | Remarks |
|---|---|---|---|---|
| Ruthenocene | 194–198 | — | vap. 85° C./0.01 mm | — |
| $Ru_3(CO)_{12}$ | 150 | 150 | — | — |
| $Ru(CO)_4$(hfb) | No m.p. data | — | Subl. at 25° C./0.05 mm Vap. 25° C./1.5 mm | Unstable above 25° C. |
| $Ru(acac)_3$ | ~223 | ~220 | — | — |
| $Ru(tfac)_3$ | 155–160 (2 isomers) | — | — | Sublimed at 85–100° C. |
| $Ru(TMHD)_3$ | 200–203 | 250 | Subl. at 120° C./0.5 mm | — |
| $Ru(TMHD)_2(COD)$ | 187–190 | 220 | subl. at 100° C./0.05 mm | — |
| $Ru(C_3H_5)_2(COD)$ | — | — | volatile at ≧50° C. | Air sensitive solid |
| $RuO_4$ | — | — | — | Highly toxic |

Accordingly, there is an urgent need for low-melting, highly volatile and relatively air and thermal stable ruthenium and osmium organometallic compounds as source reagents for various CVD applications, such as the formation of bottom electrodes, diffusion barriers, conductors, superconductors, dielectrics, capacitors, protective coating and catalytic metal alloy films. More specifically, these ruthenium source material may find applications in fabricating the four-layer $RuO_2/Ru/TiN/TiSi_x$ storage node for Gb-scale DRAM's and for manufacturing Ru pillar and $Ta_2O_5/Ru$ capacitor in embedded DRAM technology compatible to the 0.15-μm high-speed logics, whereas the osmium source reagent may find application in replacing the relatively less stable source reagent $Os(CO)_5$ for making the osmium-coated thermionic cathodes and abrasive-resistant osmium hard-coating.

It is therefore an object of the present invention to provide improved organometallic source reagents which are amenable to use in the deposition of ruthenium- and osmium-containing films.

It is another object of the present invention to provide a CVD method for forming a ruthenium- or osmium-containing film on a substrate utilizing these source reagents.

Other objects, features, and advantages will be more fully apparent from the ensuing disclosure and appended claims.

SUMMARY OF THE INVENTION

The present invention provides an organometallic source reagent for the chemical vapor deposition of ruthenium- or osmium-containing films, of the formula:

wherein

M is Ru or Os; and

L is a β-diketonate ligand $RC(O)CHC(O)R^1$ where each of R and $R^1$ is independently selected from the group consisting of atoms of the element, C, H, O and F.

In a methodological aspect, the present invention provides a method for forming a ruthenium- or osmium-containing film on a substrate, comprising the steps of:

(a) providing a precursor composition comprising an organometallic source reagent of the formula:

$$M(CO)_2L_2$$

wherein
M is Ru or Os; and
L is a β-diketonate ligand $RC(O)CHC(O)R^1$ where each of R and $R^1$ is independently selected from the group consisting of atoms of the element, C, H, O and F;

(b) volatilizing the organometallic source reagent to form a metal source vapor therefrom; and (c) contacting the metal source vapor with the substrate in a chemical vapor deposition reactor, to deposit the ruthenium- or osmium-containing film thereon.

The method of the present invention may further comprise employing a carrier gas to transport the metal source vapor to the CVD reactor.

The precursor composition may further comprise a second metal source reagent for the deposition of binary mixed-metal oxide materials such as $SrRuO_3$, $BaRuO_3$, $Sr_2RuO_4$ and $Bi_2Ru_2O_7$, or bimetallic alloys such as Pt/Ru and Pd/Ru.

Other aspects, features and embodiments of the invention will be more fully apparent from the ensuing disclosure and appended claims.

(ofac)=1,1,1,5,5,6,6,6-octafluoro-2,4-hexanedionate;
(fod)=6,6,7,7,8,8,8-heptafluoro-2,2-dimethyl-3,5-octanedionate;
(TMHD)=2,2,6,6-tetramethyl-3,5-heptanedionate;
(DMHD)=2,2-dimethyl-3,5-heptanedionate; and
(acac)=2,4-pentanedionate.

The organometallic complexes of the present invention are readily synthesized by typical organometallic synthesis techniques involving conventional procedures for forming the desired complexes. The most useful synthetic method involves the direct treatment of $Ru_3(CO)_{12}$ or $Os_3(CO)_{12}$ with six equivalents of the neutral ligand LH in a sealed stainless steel autoclave at elevated temperature, and using low boiling hydrocarbon solvent as reaction media to minimize the loss of volatile product during separation. Any other reagents that can cleanly produce the ruthenium- or osmium-containing fragment $[M(CO)_2]$ during the reaction may be employed to replace $Ru_3(CO)_{12}$ or $Os_3(CO)_{12}$ in affording the products of general formula $[M(CO)_2L_2]$. The product complexes are readily characterized using mass spectrometry (MS), nuclear magnetic resonance spectroscopy (NMR), infrared spectroscopy (IR), single crystal X-ray analysis, elemental analysis, and thermal gravimetric analysis (TGA). Selected physical properties of the organometallic source reagents of the present invention are summarized in Table 2.

TABLE 2

Physical properties of the organometallic ruthenium source reagents of the present invention

| Compound | Melting Point (° C) | Decomposition Temperature (° C.) | Vapor Pressure (torr) at 25° C. | Residual Weight (%)[d] |
|---|---|---|---|---|
| [Ru(CO)$_2$(hfac)$_2$] | 64–66 | ≧174 | 1.4 | 1.4 |
| [Ru(CO)$_2$(acac)$_2$] | 115–117 | ≧254 | 0.8 | 2.7 |
| [Ru(CO)$_2$(tfac)$_2$][a] | 55–75 | ≧236 | — | — |
| [Ru(CO)$_2$(tfac)$_2$][b] | 132–133 | ≧210 | 0.9 | 2.5 |
| [Ru(CO)$_2$(tfac)$_2$][c] | liquid | — | — | — |
| [Ru(CO)$_2$(ofac)$_2$][a] | liquid | ≧140 | 1.1 | 4.6 |
| [Ru(CO)$_2$(TMHD)$_2$] | 70–72 | ≧185 | 1.0 | 0.7 |
| [Ru(CO)$_2$(DMHD)$_2$][a] | liquid | ≧200 | — | 3.7 |
| [Os(CO)$_2$(acac)$_2$] | 145–147 | ≧280 | 0.2 | 6.9 |

[a]mixture of three structural isomers A, B and C.
[b]isomer-A only.
[c]mixture of isomer-B and isomer-C.
[d]weight percentage of the sample left at 500° C. during TGA analysis (heating rate = 10° C./min and N$_2$ flow rate =100 cm$^3$/min).

DETAILED DESCRIPTION OF THE INVENTION

The present invention generally relates to a series of organometallic complexes of the formula: $[M(CO)_2L_2]$ wherein M is ruthenium or osmium, CO is a carbonyl ligand coordinated to the metal atom, L is a bidentate β-diketonate $RC(O)CHC(O)R^1$ ligand coordinated to the metal, wherein each of two substituents R and $R^1$, which may be the same or different, is independently selected from the group consisting of atoms of the element, C, H, O and F.

Preferably, R and $R^1$ are hydrocarbyl or fluorinated hydrocarbyl groups, e.g., $CH_3$, $CH_2CH_3$, $C(CH_3)_3$, $CF_3$, $CF_2CF_3$ and $CF_2CF_2CF_3$, etc., or any other sterically acceptable and sufficiently volatile hydrocarbyl or fluorinated hydrocarbyl substituent.

Specific examples of L include:
(hfac)=1,1,1,5,5,5-hexafluoro-2,4-pentanedionate;
(tfac)=1,1,1-trifluoro-2,4-pentanedionate;

In the above-mentioned ruthenium or osmium metal complexes, when L is a bidentate β-diketonate $RC(O)CHC(O)R^1$ with $R=R^1$, only one product is isolated from the reaction. For example, when $R=R^1=CF_3$, only one structural isomer of the octahedral complex $[Ru(CO)_2(hfac)_2]$ is expected. However, when R is different from $R^1$, a mixture of three structural isomers is produced from the reaction, of which the most dominant product is an isomer (hereafter indicated as isomer-A) with both trifluoromethyl groups located at the positions trans to the carbonyl ligands. For example, when $R=CH_3$ and $R^1=CF_3$, the formation of all three possible geometrical isomers of the octahedral metal complex $[M(CO)_2(tfac)_2]$ was observed.

For the propose of using this particular type of metal complex as a CVD source reagent, no further separation of the isomeric mixture is required, as the vaporization behavior of the mixture is very similar to that of the purified, relatively high-melting isomer-A, which may be isolated by repeated recrystallization in methanol solution at a lower temperature. The liquid sample, which mainly consists of an inseparable mixture of other two isomers, can be easily isolated and purified by reduced pressure distillation of the filtrate obtained from the recrystallization process.

The above-mentioned ruthenium and osmium complexes have been found to be well suited as source reagents for CVD applications because they meet the following criteria: (1) they have high vapor pressure at temperature of below 180° C., which is essential to enable a sufficient amount of the reagent vapor to be transported into the CVD reactor at the temperature convenient for CVD processing, in an inert gas or other carrier gas stream, (2) they are thermally stable below the temperature of about 180° C., and therefore do not decompose in the CVD system, and (3) they can cleanly decompose on substrates to deposit the desired composition with little or no incorporation of carbon, oxygen and fluorine impurities.

In another aspect, the invention relates to use of the ruthenium and osmium organometallic complexes of the general formula: $[M(CO)_2L_2]$ as source reagents for CVD applications. Thus, the ruthenium and osmium organometallic complexes mentioned above may be charged into a source reservoir of a CVD reactor to deposit the ruthenium- and osmium containing thin-film materials on substrates. For liquid samples, they are introduced into the CVD reactor directly; otherwise, the temperature of sample reservoir is raised above their melting point to produce a liquid sample source. Such liquid source reagent may then be volatilized by further heating to yield a metal source vapor, and the metal source vapor may be contacted with a substrate in the CVD reactor, allowing deposition of the ruthenium- and osmium containing thin-film materials. Preferably, the reaction chamber is maintained at about 250–600° C. during the deposition process, and more preferably about 250–400° C.

Such chemical vapor deposition conditions may advantageously comprise the presence of the gaseous co-reagent or carrier gas commonly utilized in CVD applications. For example, the employment of inert gas atmosphere or a slow stream of inert carrier gas such as $N_2$, He and Ar, or a reducing carrier gas such as $H_2$, favors the formation of pure ruthenium and osmium thin films on substrates. On the other hand, the introduction of oxygen-containing atmosphere or oxidizing carrier gas such as $O_2$, $N_2O$ may lead to the formation of $Ru/RuO_2$ mixture, $Os/OsO_2$ mixture or even high purity $RuO_2$ or $OSO_2$ films at a higher deposition temperature, or upon increasing the deposition time as well as the partial pressure of the oxidizing carrier gas.

In another aspect, the present invention broadly contemplates the formation of Ru, Os, $RuO_2$, $OSO_2$, and other Ru- or Os-containing thin-films, such as mixed metal oxide materials $BaRuO_3$, $SrRuO_3$, $Sr_2RuO_4$ and $Bi_2RU_2O_7$ or bimetallic alloys Pt/Ru and Pd/Ru on substrates by CVD using the above-described ruthenium and osmium organometallic source reagents.

In accordance with the invention, the ruthenium or osmium thin film material is formed on the substrate by depositing either one of the ruthenium or osmium source reagents under inert atmosphere, such as $N_2$, He or Ar, or in the presence of reducing carrier gas such as $H_2$. The resulting ruthenium or osmium layer may be converted to $RuO_2$ or $OsO_2$ thin film in an oxygen containing atmosphere at the elevated temperature. In a like manner, the $RuO_2$ or $OSO_2$ thin film material may be prepared by depositing either one of the ruthenium or osmium source reagents on the substrate under the oxygen-containing atmosphere or under the condition where an oxygen-containing plasma is applied.

In order to constitute a mixed metal oxide layer such as $BaRuO_3$, $SrRuO_3$, $Sr_2RuO_4$ and $Bi_2Ru_2O_7$, the ruthenium source reagent must be used in combination with a second elemental constituent, which may likewise be deposited on the substrates by chemical vapor deposition from its source reagents, in the presence of oxygen-containing atmosphere. Thus, as mentioned, the second elemental constituent may comprise a β-diketonate complex of strontium, barium or bismuth. For the formation of bimetallic Pd/Ru or Pt/Ru metal alloy, the ruthenium source reagent must be used in combination with a second elemental constituent, which may also be deposited on the substrate by chemical vapor deposition from its source reagents under an inert atmosphere, reducing carrier gas or oxygen-containing atmosphere. In this case, the second elemental constituent may comprise a high volatile β-diketonate complex of palladium or platinum.

Without intending to limit it in any manner, the present invention will be further illustrated by the following examples.

EXAMPLES

Example 1

Synthesis of $[Ru(CO)_2(hfac)_2]$

Six equivalents (0.7 mL) of (hfac)H, (0.5 g) of $Ru_3(CO)_{12}$, and (50 ml) of pentane were added into a 100 ml stainless steel autoclave. The reactor was sealed under nitrogen and was then slowly heated to 170° C. After 24 hours, the solution was transferred out of the reactor, hexane solvent was evaporated under vacuum, and the residue was dissolved into minimum amount of methanol. Cooling the methanol solution to −20° C. produced 1.27 g of the light orange solid, which was collected by filtration (92%). The compound melted at 64–66° C. The $^1H$ and $^{13}C$ NMR spectra in $CDCl_3$ solution were consistent with an octahedral structure composed of two hexafluoroacetylacetonate ligands and two CO ligands arranged in cis-disposition.

Spectral data of $[Ru(CO)_2(hfac)_2]$: MS (FAB, $^{102}Ru$), m/z 572. IR $(C_6H_{12})$ : ν(CO), 2092 (s), 2036 (vs). $^1H$ NMR ($CDCl_3$, 298 K): δ6.34 (s, 2H, CH). $^{13}C$ NMR ($CDCl_3$, 298 K): δ192.5 (2C, CO), 179.1 (2C, CO, $^2J_{CF}$=36 Hz), 176.9 (2C, CO, $^2J_{CF}$=36 Hz), 116.7 (2C, $CF_3$, $^1J_{CF}$=285 Hz), 115.9 (2C, $CF_3$, $^1J_{CF}$=285 Hz), 91.8 (2C, CH). $^{19}F$ ($CDCl_3$, 298 K): δ −74.15 (s, 6F), −75.06 (s, 6F). Anal. Calcd for $C_{12}H_2F_{12}O_6Ru$: C, 25.23; H, 0.35. Found: C, 25.45; H, 0.40.

Example 2

Synthesis of $[Ru(CO)_2(acac)_2]$

The procedure of Example 1 was followed, using (acac)H as starting material rather than the (hfac)H and the pentane solvent was replaced by hexane. The autoclave was heated at 160° C. for 24 hours. After removing the hexane solvent, recrystallization of the solid residue from methanol at 4° C. gave yellow-orange crystalline solid $[Ru(CO)_2(acac)_2]$ in 85% yield. The compound melted at 115–117° C.

Spectral data of $[Ru(CO)_2(acac)_2]$: MS (EI, $^{102}Ru$): m/z 356 (M+). IR $(C_6H_{12})$: ν (CO), 2056 (s), 1988 (vs). $^1H$ NMR ($CDCl_3$, 294K): δ5.41 (s, 2H, CH), 2.04 (s, 6H, $CH_3$), 2.02 (s, 6H, $CH_3$). $^{13}C$ NMR ($CDCl_3$, 294K): δ197.5 (2C, CO), 189.9 (2C, CO), 189.0 (2C, CO), 100.6, (2C, CH), 27.8 (4C, $CH_3$). Anal. Calcd for $C_{12}H_{14}O_6Ru$: C, 40.57; H, 3.97. Found: C, 40.19; H, 4.22.

Example 3

Synthesis of $[Ru(CO)_2(TMHD)_2]$

A six-fold molar excess of (TMHD)H (1.0 mL) was added to $Ru_3(CO)_{12}$ (0.5 g) in 50 mL of hexane. Then the resulting mixture was heated to 170° C. for 24 hours, following which the volatiles were removed under vacuum. The light yellow crystalline product (1.1 g) was obtained in 90% yield by recrystallization of the residue from methanol at −20° C. This sample melted at 70–72° C.

Spectral data of [Ru(CO)$_2$(TMHD)$_2$]: MS (EI, $^{102}$Ru), m/z 524 (M$^+$). IR (C$_6$H$_{12}$): ν (CO), 2053 (s), 1985 (vs). $^1$H NMR (CDCl$_3$, 294 K): δ5.62 (s, 2H, CH), 1.09 (s, 18H, CH$_3$), 1.04 (s, 18H, CH$_3$). $^{13}$C NMR (CDCl$_3$, 294 K): δ199.1 (2C, CO), 198.4 (2C, CO), 197.0 (2C, CO), 98.6 (2C, CH), 42.1 (2C), 41.1 (2C), 28.7 (6C, CH$_3$), 28.5 (6C, CH$_3$). Anal. Calcd for C$_{24}$H$_{38}$O$_6$Ru: C, 55.05; H, 7.31. Found: C, 55.37; H, 7.53.

Example 4
Synthesis of [Ru(CO)$_2$(tfac)$_2$]

A six-fold molar excess of (tfac)H (1.71 g) was added to Ru$_3$(CO)$_{12}$ (0.8 g) in 50 mL of hexane. The resulting mixture was heated to 170° C. for 24 hours, following which the volatiles were removed under vacuum. The yellow-orange solid product (1.5 g), which consists of three structural isomers, was obtained in 87% yield by reduced pressure distillation at 120° C. and at 500 mtorr using a Buchi GKR-51 distillation apparatus.

Selected spectral data of [Ru (CO)$_2$(tfac)$_2$]: MS (EI, $^{102}$Ru): m/z 464 (M$^+$). IR (C$_6$H$_{12}$): ν (CO), 2073 (s), 2011 (vs).

Light yellow crystalline product, which consists of the single isomer-A with melting point 132–133° C., was obtained by repeated recrystallization from methanol solution at room temperature.

Spectral data of the isomer-A of [Ru(CO)$_2$(tfac)$_2$]: MS (EI, $^{102}$Ru): m/z 464 (M$^+$). IR (C$_6$H$_{12}$): ν (CO), 2073(s), 2011 (vs). $^{13}$H NMR (CDCl$_3$, 294K): δ5.85 (s, 2H, CH), 2.21 (s, 6H, CH$_3$) $^{13}$C NMR (CDCl$_3$, 298 K): δ198.4 (2C, CO), 195.2 (2C, CO), 169.0 (q, 2C, $^2J_{CF}$=34 Hz), 118.0 (q, 2C, $^1J_{CF}$=283 Hz), 95.8 (2C, CH), 28.9 (2C, CH$_3$). $^{19}$F (CDCl$_3$, 298K): δ−74.44 (s, 6F). Anal. Calcd for C$_{12}$H$_8$F$_6$O$_6$Ru: C, 31.11; H, 1.74. Found: C, 31.30; H, 1.52.

A yellow-orange viscous liquid, which is composed of an inseparable mixture of two other isomers B and C and a very small amount of the isomer-A, was obtained from reduced pressure distillation of the filtrate that was collected during recrystallization.

Selected spectral data of a mixture of isomer-B and C in an approximate 2:1 ratio. Isomer-B: $^1$H NMR (CDCl$_3$, 294K): δ5.90 (s, 1H, CH), 5.87 (s, 1H, CH), 2.21 (s, 3H, CH$_3$), 2.21 (s, 3H, CH$_3$). $^{19}$F (CDCl$_3$, 298K): δ−73.75 (s, 3F), −74.57 (s, 3F). Isomer-C: $^1$H NMR (CDCl$_3$, 294K): δ5.88 (s, 2H, CH), 2.23 (s, 6H, CH$_3$). $^{19}$F (CDCl$_3$, 298K): δ−73.70 (s, 6F).

Example 5
Synthesis of [Ru(CO)$_2$(ofac)$_2$]

A six-fold molar excess of (ofac)H (5.0g) was added to Ru$_3$(CO)$_{12}$ (1.76 g) in 50 mL of hexane. The resulting mixture was heated to 170° C. for 24 hours, following which the volatiles were removed under vacuum. The yellow orange viscous liquid (1.87 g), which consists of all three possible structural isomers, was obtained in 33% yield by reduced pressure distillation at 120° C. and at 500 mtorr.

Example 6
Synthesis of [Os(CO)$_2$(acac)$_2$]

A six equivalent (0.35 mL) of (acac)H, (0.5 g) of Os$_3$(CO)$_{12}$, and (50 ml) of hexane were added into a 100 ml stainless steel autoclave. The reactor was sealed under nitrogen and was then slowly heated to 185° C. for 36 hours. After removing the hexane solvent, distillation of the product residue at 150° C. and at 780 mtorr gave light yellow solid [Os(CO)$_2$(acac)$_2$] in 30% yield. The compound melted at 145–147° C.

Spectral data of [Os(CO)$_2$(acac)$_2$]: MS (EI, $^{192}$Os): m/z 446 (M$^+$). IR (C$_6$H$_{12}$): ν (CO), 2034 (s), 1957 (vs). $^1$H NMR (CDCl$_3$, 294K): δ5.50 (s, 2H, CH), 2.08 (s, 6H, CH$_3$), 2.00 (s, 6H, CH$_3$). $^{13}$C NMR (CDCl$_3$, 294K): δ189.1 (2C, CO), 187.4 (2C, CO), 178.8 (2C, CO), 101.9, (2C, CH), 27.2 (2C, CH$_3$), 26.9 (2C, CH$_3$). Anal. Calcd for C$_{12}$H$_{14}$O$_6$Os: C, 32.43; H, 3.18. Found: C,32.36; H, 3.22.

Example 7
CVD of ruthenium metal thin-film

Typically, ruthenium metal thin-film may be prepared by chemical vapor deposition at about 300–500° C. and about 2000–400 mtorr in a typical cold-wall reactor. In this example, the complexes [Ru(CO)$_2$(hfac)$_2$], [Ru(CO)$_2$(tfac)$_2$] and [Ru(CO)$_2$(TMHD)$_2$] were used as the sources reagents and the run conditions are listed in Table 3. Growths of smooth metallic thin films were realized on Si wafer, Pyrex glass and Al$_2$O$_3$ substrates. The deposited films were found to be highly reflective with good adhesion to all substrates. The composition of the film was determined by Auger/ESCA analysis. For a Ru thin-film prepared from [Ru(CO)$_2$(hfac)$_2$] as source reagent, the presence of 95% of ruthenium, alone with 2% of fluorine and 3% of oxygen impurities was observed, but the amount of carbon impurity is below the detection limit. Electrical conductivity measurement of the films in one example give a resistivity of 48 μΩ-cm, which is higher than that of bulk ruthenium (16 μΩ-cm). This may be attributed to the incorporation of fluorine and oxygen impurities in the ruthenium films and poor connectivity between grains in the film.

For a Ru thin-film prepared from [Ru(CO)$_2$(TMHD)$_2$] as source reagent, a bright and adherent thin-film containing over 97% of Ru metal was prepared by using H$_2$ as carrier gas. No fluorine contamination was observed in the thin-film as the precursor possessing no fluorine atom on the β-diketonate ligands. Upon changing the carrier gas to O$_2$, a relatively dark, adherent thin-film involving a mixture of Ru and RuO$_2$ was obtained, which was highlighted by the detection of substantial amount of oxygen.

While the invention has been particularly shown and described with reference to the preferred embodiment thereof, it will be understood by those skilled in the art that various changes in form and details may be made without departing from the spirit and scope of the invention.

TABLE 3

Deposition condition of CVD experiments using the organometallic ruthenium source reagents of the present invention

| Compound | Evaporation Temp. (° C.) | Deposition Temp. (° C.) | Carrier Gas | Reactor Pressure (torr) | Substrate | Film Compositions |
|---|---|---|---|---|---|---|
| [Ru(CO)$_2$(hfac)$_2$] | 30 | 500 | none | 0.5 | Si, SiO$_2$; Al$_2$O$_3$ | Ru, 95%; O, 3%; F, 2%. |
| [Ru(CO)$_2$(hfac)$_2$] | 30 | 400 | O$_2$ | 1 | Si, SiO$_2$; Al$_2$O$_3$ | Ru, 52%; O, 42%; F, 6%. |

TABLE 3-continued

Deposition condition of CVD experiments using the organometallic ruthenium source reagents of the present invention

| Compound | Evaporation Temp. (° C.) | Deposition Temp. (° C.) | Carrier Gas | Reactor Pressure (torr) | Substrate | Film Compositions |
|---|---|---|---|---|---|---|
| [Ru(CO)$_2$(tfac)$_2$] | 50 | 350 | H$_2$ | 0.5 | Si | Ru, 94%; O, 2%. F, 4%. |
| [Ru(CO)$_2$(TMHD)$_2$] | 70 | 400 | H$_2$ | 0.2 | Si | Ru, 97%; O, 3%. |
| [Ru(CO)$_2$(TMHD)$_2$] | 70 | 300 | O$_2$ | 1 | Si | Ru, 65%; O, 35%. |

What is claimed is:

1. An organometallic source reagent for the chemical vapor deposition of ruthenium- or osmium-containing films, of the formula:

$$M(CO)_2L_2$$

wherein

M is Ru or Os; and

L is a β-diketonate ligand RC(O)CHC(O)R$^1$ where each of R and R$^1$ is independently selected from the group consisting of hydrocarbyl groups optionally substituted with fluorine or oxygen atoms;

provided that when M is Ru, L is not 2,4 pentanedionate.

2. The organometallic source reagent as claimed in claim 1, wherein each of R and R$^1$ is independently hydrocarbyl or fluorinated hydrocarbyl functional group.

3. The organometallic source reagent as claimed in claim 1, wherein M is Ru; and L is selected from the group consisting of 1,1,1,5,5,5-hexafluoro-2,4-pentanedionate (hfac); 1,1,1-trifluoro-2,4-pentanedionate (tfac); 1,1,1,5,5,6,6,6-octafluoro-2,4-hexanedionate (ofac); 6,6,7,7,8,8,8-heptafluoro-2,2-dimethyl-3,5-octanedionate (fod); 2,2,6,6-tetramethyl-3,5-heptanedionate(TMHD); and 2,2-dimethyl-3,5-heptanedionate (DMHD).

4. The organometallic source reagent as claimed in claim 1, wherein M is Os; and L is selected from the group consisting of hfac; tfac; ofac; fod; TMHD; DMHD; and 2,4-pentanedionate (acac).

5. The organometallic source reagent as claimed in claim 1, wherein said organometallic source reagent is selected from the group consisting of RU(CO)$_2$(hfac)$_2$, Ru(CO)$_2$(tfac)$_2$, Ru(CO)$_2$(TMHD)$_2$, Ru(CO)$_2$(DMHD)$_2$, and Os(CO)$_2$(acac)$_2$.

6. The organometallic source reagent as claimed in claim 1, wherein said organometallic source reagent is Ru(CO)$_2$(hfac)$_2$.

7. The organometallic source reagent as claimed in claim 1, wherein said organometallic source reagent is Ru(CO)$_2$(TMHD)$_2$.

8. An organometallic source reagent for the chemical vapor deposition of ruthenium- or osmium-containing films, of the formula:

$$M(CO)_2L_2$$

wherein

M is Ru or Os; and

L is selected from the group consisting of hfac; tfac; ofac; fod; TMHD and DMHD.

* * * * *